United States Patent [19]

Tsujii et al.

[11] Patent Number: 4,983,749
[45] Date of Patent: * Jan. 8, 1991

[54] PROCESS FOR PREPARING A S-SUBSTITUTED PHOSPHORO-CHLORIDOTHIOLATE

[75] Inventors: Tasuhiro Tsujii; Tatsuo Isogai; Takao Awazu; Tokiya Kimura, all of Kusatsu, Japan

[73] Assignee: Ishihara Sangyo Kaisha Ltd., Osaka, Japan

[ * ] Notice: The portion of the term of this patent subsequent to Apr. 5, 2005 has been disclaimed.

[21] Appl. No.: 144,230

[22] Filed: Jan. 15, 1988

Related U.S. Application Data

[63] Continuation-in-part of Ser. No. 916,106, Oct. 7, 1986, Pat. No. 4,736,050.

[30] Foreign Application Priority Data

Oct. 17, 1985 [JP] Japan ............................. 60-232168

[51] Int. Cl.$^5$ ............................................. C07F 9/02
[52] U.S. Cl. ............................................. 558/88
[58] Field of Search ............................................. 558/88

[56] References Cited

U.S. PATENT DOCUMENTS 4,736,050 4/1988 Tsajii et al. ............................. 558/88

FOREIGN PATENT DOCUMENTS 219770 4/1987 European Pat. Off. ............... 558/88

OTHER PUBLICATIONS

Nifantiev, "Chemistry of Phosphorus-Organic Compounds," Moscow Univ. Pub., (1971), pp. 174 and 209.
J. Org. Chem., vol. 41, No. 7, 1976, pp. 1291-1293.

Primary Examiner—Mukund J. Shah
Assistant Examiner—C. L. Cseh
Attorney, Agent, or Firm—Oblon, Spivak, McClelland, Maier & Neustadt

[57] ABSTRACT

A process for preparing a S-substituted phosphoro-chloridothiolate having the formula:

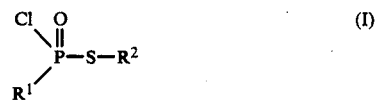

(I)

wherein $R^1$ is a chlorine atom or an alkoxy or phenoxy group which may be substituted, and $R^2$ is an alkyl, alkenyl, alkynyl, cycloalkyl or phenyl group which may be substituted, which comprises isomerizing an O-substituted phosphorochloridothionate having the formula:

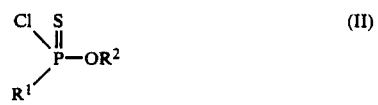

(II)

wherein $R^1$ and $R^2$ are as defined above, in the presence of a Lewis acid catalyst or a phosphorus compound catalyst.

10 Claims, No Drawings

PROCESS FOR PREPARING A S-SUBSTITUTED PHOSPHORO-CHLORIDOTHIOLATE

This application is a continuation-in-part application of application Ser. No. 06/916,106 having a filng date of Oct. 7, 1986, now U.S. Pat. No. 4,736,050.

The present invention relates to a process for producing a S-substituted phosphorochloridothiolate (hereinafter referred to simply as SPO) by isomerizing an O-substituted phosphorochloridothionate (hereinafter referred to simply as OPS) in the presence of a specific catalyst.

From the viewpoint for the preparation of SPO, conventional processes for the production of S-substituted phosphorodichloridothioates are as follows. For instance, Japanese Unexamined Patent Publication No. 206393/1984 and Swiss Patent No. 1,097,631 disclose processes in which S-methyl phosphorodichloridothiolate is obtained by isomerizing an O-methyl phosphorodichloridothionate in the presence of a quaternary ammonium salt or in the presence of an amine catalyst as a copolymer of 2-methyl-5-vinylpyridine with divinyl benzene. These processes have a drawback that their application is limited to O-methyl phosphorodichloridothionate.

Further, Journal für praktische Chemie., 4 Reihe Band 12 (1960) discloses a process in which O-methyl phosphorodichloridothionate is subjected to thermal isomerization in the absence of a solvent at a reaction temperature of from 100° to 110° C. to obtain S-methyl phosphorodichloridothiolate. However, this process has drawbacks that the control of the reaction is difficult, and the yield is low.

Japanese Unexamined Patent Publication No. 31033/1977 discloses a process wherein a sulfenyl chloride, phosphorus trichloride and water or a carboxylic acid are reacted to obtain a S-substituted phosphorodichloridothiolate. However, this process has drawbacks that an expensive sulfenyl chloride is used as the starting material, and the reaction steps are cumbersome.

On the other hand, SPO has been useful as an intermediate material for active ingredients of various agricultural chemicals, and it is strongly desired to develop an industrially advantageous process for its production.

The present inventors have conducted extensive researches for the production of SPO, and as a result, have found it possible to produce SPO industrially advantageously by a novel process which has not been disclosed in the above-mentioned literatures.

A primary object of the present invention is to provide an industrial process for the production of SPO.

The second object of the present invention is to provide a process for industrially advantageously producing SPO from an inexpensive starting material by using a simple reaction.

Other objects of the present invention will be apparent from the following description of the present invention.

The present invention provides a process for preparing a S-substituted phosphorochloridothiolate having the formula:

wherein $R^1$ is a chlorine atom or an alkoxy or phenoxy group which may be substituted, and $R^2$ is an alkyl, alkenyl, alkynyl, cycloalkyl or phenyl group which may be substituted, which comprises isomerizing an O-substituted phosphorochloridothionate having the formula:

wherein $R^1$ and $R^2$ are as defined above, in the presence of a Lewis acid catalyst or a phosphorus compound catalyst.

Now, the present invention will be described in detail with reference to the preferred embodiments.

In the formulas I and II, the substituent for the substituted alkoxy group as $R^1$ or for the substituted alkyl, alkenyl, alkynyl or cycloalkyl group as $R^2$ may be any substituent so long as it does not adversely affect the reaction. For instance, it may be a phenyl, phenoxy or phenylthio group which may be substituted. The substituted group may have only one such a substituent or may have two or more substituents which may be the same or different.

The substituted phenyl, phenoxy or phenylthio group as $R_1$, $R_2$ or such a substituent, may have only one substituent or two or more substituents which may be the same or different, so long as they do not adversely affect the reaction for the process of the present invention. As such substituents, there may be mentioned a halogen atom; a nitro group; a cyano group; an alkyl group; an alkoxy group; an alkoxyalkyl group; a trifluoromethyl group; a haloalkoxy group such as trifluoromethoxy or trifluoroethoxy; an alkylsulfinyl group; an alkylsulfonyl group; and a phenyl, phenoxy or phenylthio group which may be substituted by halogen, nitro, cyano, trifluoromethyl, trifluoroethoxy, alkyl or alkoxy.

The alkyl group and the alkyl moiety constituting the above-mentioned groups or substituents as $R_1$, $R_2$ or such a substituent, may have from 1 to 6 carbon atoms. For instance, methyl, ethyl, n-propyl, iso-propyl, n-butyl, sec-butyl, iso-butyl, tert-butyl, n-pentyl and n-hexyl may be mentioned. The alkenyl group as $R^2$ may have from 2 to 6 carbon atoms. For instance, ethenyl, propenyl, butenyl and pentenyl may be mentioned. Likewise, the alkynyl group may have from 2 to 6 carbon atoms For instance, ethyne, propyne, butyne and pentyne may be mentioned.

The cycloalkyl group as $R^2$ may have from 3 to 7 carbon atoms. For instance, it includes cyclopropyl, cyclobutyl, cyclopentyl, cyclohexyl and cycloheptyl may be mentioned.

The halogen atom for the above-mentioned substituent or as a constituent for such a substituent includes chlorine, fluorine, bromine and iodine.

In the formulas I and II, Rl is preferably a chlorine atom or a $C_1$–$C_6$ alkoxy group, more preferably a chlorine atom. Likewise, $R^2$ is preferably a $C_1$–$C_6$ alkyl group, a $C_2$-$C_6$ alkenyl group, a $C_2$-$C_6$ alkynyl group or a $C_3$-$C_7$ cycloalkyl group which may be substituted, more preferably a $C_1$-$C_6$ alkyl group, a $C_1$-$C_6$ alkenyl group or a $C_2$-$C_6$ alkynyl group which may be substituted, most preferably a $C_1$-$C_6$ alkyl group which may be substituted.

The Lewis acid catalyst to be employed in the present invention includes inorganic Brønsted acids such as sulfuric acid, chlorosulfonic acid, fluorosulfonic acid, hydrochloric acid, hydrogen bromide, hydrogen fluoride, hydrogen iodide, hydrogen sulfide, nitric acid, boric acid, pyrosulfuric acid and phosphoric acid; and metal halides such as boron trifluoride, aluminum fluoride, aluminum chloride, aluminum bromide, tin tetrachloride, zinc chloride, titanium tetrachloride, ferric chloride, antimony trichloride and antimony pentachloride. The phosphorus compound catalyst includes inorganic phosphorus oxides or halides, such as phosphorus pentoxide, phosphorus pentachloride and phosphorus oxychloride. Among such catalysts, Bronsted acids are advantageous and practically superior to metal halides from the point of view of costs and after-treatment. Among such Bronsted acids, sulfuric acid is preferred. Likewise, among metal halides, ferric chloride and aluminum chloride are preferred.

These catalysts may be used alone or in combination or as a mixture. The amount of the catalyst is usually from 5 to 300 mol %, preferably from 10 to 200 mol%, relative to 1 mol of OPS. If the amount of the catalyst is less than the above range, the reaction tends to hardly proceed. On the other hand, if the amount exceeds the above range, there is no substantial improvement in the reactivity, and such an excessive use is economically disadvantageous. The reaction is conducted usually within the range of from $-20°$ to $150°$ C., preferably from -10 to $100°$ C. If the reaction temperature exceeds the above range, by-products tend to increase, thus leading to a deterioration in the yield. On the other hand, if the temperature is lower than the above range, the yield of the reaction tends to deteriorate, such as being practically disadvantageous.

The reaction time in the process of the present invention varies depending upon the types of the starting materials, the reaction conditions, etc., but is usually from 0.1 to 10 hours.

The process of the present invention may be conducted in the presence of an inert diluent. As such an inert diluent, an aromatic hydrocarbon such as benzene, nitrobenzene, toluene or xylene, a ketone such as acetone or methyl isobutyl ketone, an ether such as diethyl ether or diisopropyl ether, and an aliphatic halogenated hydrocarbon such as methylene chloride, chloroform or carbon tetrachloride may be mentioned. Among them, an aromatic hydrocarbon and an aliphatic halogenated hydrocarbon such as benzene, chlorobenzene, nitrobenzene and carbon tetrachloride, are preferred.

Now, the process of the present invention will be described in further detail with reference to Examples. However, it should be understood that the present invention is by no means restricted to these specific Examples.

EXAMPLE 1

Into a 200 ml four-necked flask equipped with a stirrer, a thermometer and a reflux condenser, 90 g of O-sec-butyl phosphorodichloridothionate was charged, and 44 g of concentrated sulfuric acid (96%) was dropwise added over a period of 30 minutes under stirring and cooling with water. Then, the reaction system was stirred at $20°$ C. for 3 hours.

After the reaction, a part of the reaction product was sampled and analyzed for the composition by gas chromatography, whereby the yield of S-sec-butyl phosphorodichloridothiolate was 99.7%.

Then, the reaction product was poured into 600 ml of ice water, and then 400 ml of methylene chloride was added for extraction.

After the extraction, the methylene chloride layer was dried over anhydrous sodium sulfate. Then, methylene chloride was distilled off under reduced pressure, and distillation was conducted to obtain 80.8 g of S-sec-butyl phosphorodichloridothiolate having a boiling point of $95°$-$96°$ C./15 mmHg. The yield was 89.8%.

EXAMPLE 2

Into a 20 ml four-necked flask equipped with a stirrer and a thermometer, 0.6 g of anhydrous ferric chloride and 2 ml of carbon tetrachloride as an inert diluent, were charged, and 4 g of O-sec-butyl phosphorodichloridothionate was dropwise added thereto under stirring and cooling with water. Then, the reaction was conducted for 2 hours while maintaining the temperature at a level of from $50°$ to $60°$ C.

After the completion of the reaction, a part of the reaction solution was sampled and analyzed for the composition by gas chromatography, whereby the yield of S-sec-butyl phosphorodichloridothiolate was 97.7%.

EXAMPLES 3 to 26

By using the starting materials and catalysts as identified in the following table, isomerization was conducted in the same manner as in Example 2. The results thereby obtained are shown in the following table.

TABLE

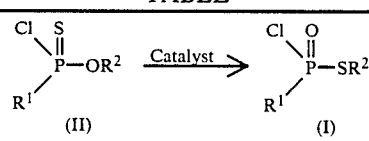

| Example No. | $R^1$ | Compound of the formula II $R^2$ | Amount of catalyst (Mol % per mol of Compound II) | Reaction temp. (°C.) | Reaction time (hr) | Composition of reaction product (%) Cl,S / P—OR² / R¹ | Cl,O / P—SR² / R¹ | Cl,S / P—SR² / R¹ | Physical properties of obtained Compound I BP (°C.)/ mmHg |
|---|---|---|---|---|---|---|---|---|---|
| 3 | Cl | —CH$_3$ | H$_2$SO$_4$ (200) | 30–40 | 1.5 | — | 95.5 | 0.8 | 65–66/11 |
| 4 | Cl | —C$_2$H$_5$ | H$_2$SO$_4$ (150) | 40–50 | 0.5 | 0.6 | 88.1 | — | 78–79/15 |
| 5 | Cl | n-C$_3$H$_7$— | H$_2$CO$_4$ (200) | 25 | 2 | — | 81.5 | 12.5 | 105–110/15 |

TABLE -continued $$\begin{array}{c} Cl\quad S \\ \diagdown\;\|\; \\ P\!-\!OR^2 \\ \diagup \\ R^1 \\ (II) \end{array} \xrightarrow{\text{Catalyst}} \begin{array}{c} Cl\quad O \\ \diagdown\;\|\; \\ P\!-\!SR^2 \\ \diagup \\ R^1 \\ (I) \end{array}$$

| Example No. | $R^1$ | Compound of the formula II $R^2$ | Amount of catalyst (Mol % per mol of Compound II) | Reaction temp. (°C.) | Reaction time (hr) | Composition of reaction product (%) $\begin{array}{c} Cl\;\;S\\ \diagdown\;\|\\ P\!-\!OR^2\\ \diagup\\ R^1 \end{array}$ | $\begin{array}{c} Cl\;\;O\\ \diagdown\;\|\\ P\!-\!SR^2\\ \diagup\\ R^1 \end{array}$ | $\begin{array}{c} Cl\;\;S\\ \diagdown\;\|\\ P\!-\!SR^2\\ \diagup\\ R^1 \end{array}$ | Physical properties of obtained Compound I BP (°C.)/mmHg |
|---|---|---|---|---|---|---|---|---|---|
| 6 | Cl | iso-$C_3H_7$— | $H_2SO_4$ (200) | 25 | 1.5 | 0.3 | 98.9 | — | 52–56/4 |
| 7 | Cl | n-$C_4H_9$— | $H_2SO_4$ (200) | 35 | 1 | 4.0 | 77.8 | 17.5 | 115–120/17 |
| 8 | Cl | sec-$C_4H_9$— | $H_2SO_4$ (100) | 25 | 2.5 | 0.2 | 99.7 | 0.1 | 95–96/15 |
| 9 | Cl | iso-$C_3H_7$— | $FeCl_3$ (50) | 25 | 0.5 | 1.0 | 98.5 | 0.5 | 52–56/4 |
| 10 | Cl | sec-$C_4H_9$— | HBr (50) | 60 | 4.3 | 34 | 60 | 5 | 95–96/15 |
| 11 | Cl | sec-$C_4H_9$— | $AlCl_3$ (100) | 25 | 2 | — | 96.5 | 0.7 | 95–96/15 |
| 12 | Cl | sec-$C_4H_9$— | $FeCl_3$ (50) | 25 | 1 | — | 93.9 | 2.4 | 95–96/15 |
| 13 | Cl | sec-$C_4H_9$— | $ZnCl_2$ (100) | 60 | 2 | 0.6 | 89.7 | 7.2 | 95–96/15 |
| 14 | Cl | sec-$C_4H_9$— | $TiCl_4$ (100) | 25 | 2 | — | 67.8 | 0.1 | 95–96/15 |
| 15 | Cl | sec-$C_4H_9$— | $SbCl_5$ (100) | 25 | 1 | — | 55.3 | 0.5 | 95–96/15 |
| 16 | Cl | sec-$C_4H_9$— | $BE_3$-ether complex (146) | 60–70 | 2 | 3.9 | 87.9 | — | 95–96/15 |
| 17 | Cl | sec-$C_4H_9$— | $PCl_5$ (100) | 100 | 2 | 0.9 | 67.3 | 2.8 | 95–96/15 |
| 18 | Cl | sec-$C_4H_9$— | $P_2O_5$ (100) | 60 | 3 | 2.2 | 82.9 | 1.3 | 95–96/15 |
| 19 | Cl | sec-$C_4H_9$— | $POCl_3$ (100) | 100 | 3 | 2.3 | 82.7 | 11.5 | 95–96/15 |
| 20 | Cl | sec-$C_4H_9$— | $H_3BO_3$ (100) | 100 | 1 | 43.3 | 49.1 | 0.1 | 95–96/15 |
| 21 | Cl | —$CH_2CH\!=\!CH_2$ | $H_2SO_4$ (100) | 25 | 2 | 1.4 | 90.9 | — | 90–92/14 |
| 22 | Cl | —$CH_2CH_2$—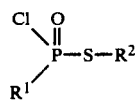 | $FeCl_3$ (100) | 25 | 1.0 | 7.7 | 39.1 | — | 130–135/3 |
| 23 | Cl | 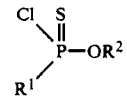—$OCH_3$ | $FeCl_3$ (100) | 50 | 0.5 | 26.6 | 37.2 | 26.5 | 155–160/5 |
| 24 | Cl | —⟨H⟩ | $H_2SO_4$ (150) | 25 | 1.0 | 0.3 | 97.4 | — | |
| 25 | —$OCH_3$ | —$CH_3$ | $H_2SO_4$ (220) | 50 | 1.5 | — | 98.3 | — | 83/11 |
| 26 | —$OC_2H_5$ | —$C_2H_5$ | $H_2SO_4$ (220) | 35 | 1.5 | — | 90.0 | — | 78/6 |

COMPARATIVE EXMAPLE

To 5 ml of toluene, 0.21 g of benzyl trimethylammonium iodide was added, and 4 g of O-sec-butyl phosphorodichloridothionate was dropwise added thereto at 60° C. over a period of 30 minutes under stirring. The reaction system was stirred at the same temperature for 4 hours. Then, the reaction product was sampled and analyzed by gas chromatography, whereby no formation of desired S-sec-butyl phosphorodichloridothiolate was observed, and the starting material remained unreacted. Further, the stirring was continued at the same temperature for 10 hours, and then a similar analysis was conducted, whereby no formation of S-sec-butyl phosphorodichloridothiolate was observed.

What is claimed as new and desired to be secured by Letters Patent of the United States is:

1. A process for the preparation of a S-substituted phosphorochloridothiolate having the formula:

$$\begin{array}{c} Cl\quad O \\ \diagdown\;\|\; \\ P\!-\!S\!-\!R^2 \\ \diagup \\ R^1 \end{array}$$

wherein $R^1$ is selected from the group consisting of chloro, phenoxy, $C_1$–$C_6$ alkoxy, and $C_1$–$C_6$ alkoxy which is substituted by phenyl, phenoxy or phenylthio and wherein said phenyl, phenoxy and phenylthio substituents are unsubstituted or are each substituted by halogen, nitro, cyano, $C_1$–$C_6$ alkyl, $C_1$–$C_6$ alkoxy, $C_1$–$C_6$ alkoxy-$C_1$–$C_6$ alkyl, trifluoromethyl, halo-$C_1$–$C_6$-alkoxy, $C_1$–$C_6$-alkylsulfinyl, $C_1$–$C_6$-alkylsulfonyl, phenyl, phenoxy or phehylthio; and $R^2$ is selected from the group consisting of phenyl, $C_1$–$C_6$-alkyl, $C_2$–$C_6$ alkenyl, $C_2$–$C_6$-alkynyl, and $C_3$–$C_7$-cycloalkyl; and wherein each of said alkyl, alkenyl, alkynyl and cycloalkyl groups are unsubstituted or substituted by phenyl, phenoxy or phenylthio; and wherein each of said phenyl, phenoxy or phenylthio substituents are unsubstituted or are substituted by halogen, nitro, cyano, $C_1$–$C_6$ alkyl, $C_1$–$C_6$ alkoxy, $C_1$–$C_6$-alkoxy-$C_1$–$C_6$-alkyl, trifluoromethyl, halo-$C_1$–$C_6$-alkoxy, $C_1$–$C_6$alkylsulfinyl, $C_1$–$C_6$alkylsulfonyl, phenyl, phenoxy and phenylthio; which process comprises:

subjecting an O-substituted phosphorochloridothionate having the formula:

$$\begin{array}{c} Cl\quad S \\ \diagdown\;\|\; \\ P\!-\!OR^2 \\ \diagup \\ R^1 \end{array}$$

wherein $R^1$ and $R^2$ are as defined above, to a Lewis acid catalyst, thereby isomerizing said O-substituted phosphorochloridothionate to said S-substituted phosphorochloridothiolate; wherein said Lewis acid catalyst is (A) a Bronsted acid selected from the group consisting of sulfuric acid, chlorosulfonic acid, fluorosulfonic acid, hydrochloric acid, hydrogen bromide, hydrogen fluoride, hydrogen iodide, hydrogen sulfide, nitric acid, boric acid, pyrosulfuric acid and phosphoric acid, or (B) a metal halide selected from the group consisting of boron trifluoride, aluminum fluoride, aluminum chloride, aluminum bromide, tin tetrachloride, zinc chloride, titanium tetrachloride, ferric chloride, antimony trichloride and antimony pentachloride.

2. (Amended) The process according to claim 1, wherein $R^1$ is a chlorine atom or a $C_1$–$C_6$ alkoxy group, and $R^2$ is a $C_1$–$C_6$ alkyl group, $C_2$–$C_6$ alkenyl group, $C_2$–$C_6$ alkynyl group or a $C_3$–$C_7$ cyclohexyl group.

3. The process according to claim 2, wherein $R^1$ is a chlorine atom, and $R^2$ is a $C_1$–$C_6$ alkyl group, a $C_2$–$C_6$ alkenyl group or a $C_2$–$C_6$ alkynyl group.

4. The process according to claim 2, wherein $R^1$ is a chlorine atom, and $R^2$ is a $C_1$–$C_6$ alkyl group.

5. The process according to claim 1, wherein the Bronsted acid is selected from the group consisting of sulfuric acid, chlorosulfonic acid, fluorosulfonic acid, hydrochloric acid, hydrogen bromide, hydrogen fluoride, hydrogen iodide, nitric acid, boric acid, pyrosulfuric acid, phosphoric acid and hydrogen sulfide.

6. The process according to claim 1, wherein the Bronsted acid is sulfuric acid.

7. The process according to claim 1, wherein the metal halide is selected from the group consisting of boron trifluoride, aluminum fluoride, aluminum chloride, aluminum bromide, tin tetrachloride, titanium tetrachloride, zinc chloride, ferric chloride, antimony trichloride and antimony pentachloride.

8. The process according to claim 1, wherein the metal halide is ferric chloride or aluminum chloride.

9. The process according to claim 1, wherein the isomerization is conducted at a temperature of from −20° to 150° C.

10. The process according to claim 1, wherein the catalyst is used in an amount of from 5 to 300 mol% relative to 1 mol of the O-substituted phosphorochloridothionate.

* * * * *